United States Patent [19]

Tsutsui et al.

[11] Patent Number: 5,132,480
[45] Date of Patent: Jul. 21, 1992

[54] HYDRODEALKYLATION PROCESS

[75] Inventors: Toshio Tsutsui; Osamu Kubota; Toshihito Nakamura, all of Chiba, Japan

[73] Assignee: Fuji Oil Company, Ltd., Tokyo, Japan

[21] Appl. No.: 475,213

[22] Filed: Feb. 5, 1990

[30] Foreign Application Priority Data

Feb. 6, 1989 [JP] Japan .................................. 1-27220
May 18, 1989 [JP] Japan ................................ 1-125364

[51] Int. Cl.$^5$ .......................... C07C 4/12; B01J 20/34
[52] U.S. Cl. ................................. 585/489; 585/488; 585/485; 502/41
[58] Field of Search ....................... 585/489, 488, 485; 502/41

[56] References Cited

U.S. PATENT DOCUMENTS

| | | | |
|---|---|---|---|
| 3,204,006 | 8/1965 | Broughton | 585/485 |
| 4,247,730 | 1/1981 | Brunelle | 585/489 |
| 4,490,243 | 12/1984 | Miyauchi et al. | 208/127 |
| 4,772,378 | 9/1988 | Miyauchi et al. | 208/107 |

FOREIGN PATENT DOCUMENTS

| | | | |
|---|---|---|---|
| 70-09661 | 3/0019 | Japan | 585/489 |
| 52-009661 | 3/1977 | Japan | 585/489 |

OTHER PUBLICATIONS

*Bethea et al.,* Ind. Eng. Chem., vol. 50, No. 9, Sep. 1985, pp. 1245-1252, "Production of Aromatics by Hydrodealkylation".
*Ind. Eng. Chem.,* "Hydrodealkylation Process", vol. 54 (1962), pp. 28-33.
N. E. Ockerbloom, *Hydrocarbon Processing,* "Xylenes and Higher Aromatics", Dec. 1971, pp. 101-105.
American National Standard *ASTM D 975-78,* "Standard Specification for Diesel Oil Fuels" (1978) (p. 2).
Gary et al, "Petroleum Refining," pp. 5-15.
"Kirk-Othmer Encyclopedia of Chemical Technology," vol. 11, pp. 682-684 (1982).
"Kirk-Othmer Encyclopedia of Chemical Technology," vol. 17, pp. 183-191 and 200-205 (1982).
G. H. Unzelman, *Oil and Gas J.,* "Higher Diesel Quality would Constrict Refining," Jun. 29, 1987, pp. 55-59.

*Primary Examiner*—Asok Pal
*Assistant Examiner*—Nhat Phan
*Attorney, Agent, or Firm*—Oblon, Spivak, McClelland, Maier & Neustadt

[57] ABSTRACT

Catalytic hydrodealkylation by means of a catalyst which comprises microporous particles having a catalytic species carried thereon. Particulars of the microporous particles are disclosed.

10 Claims, 1 Drawing Sheet

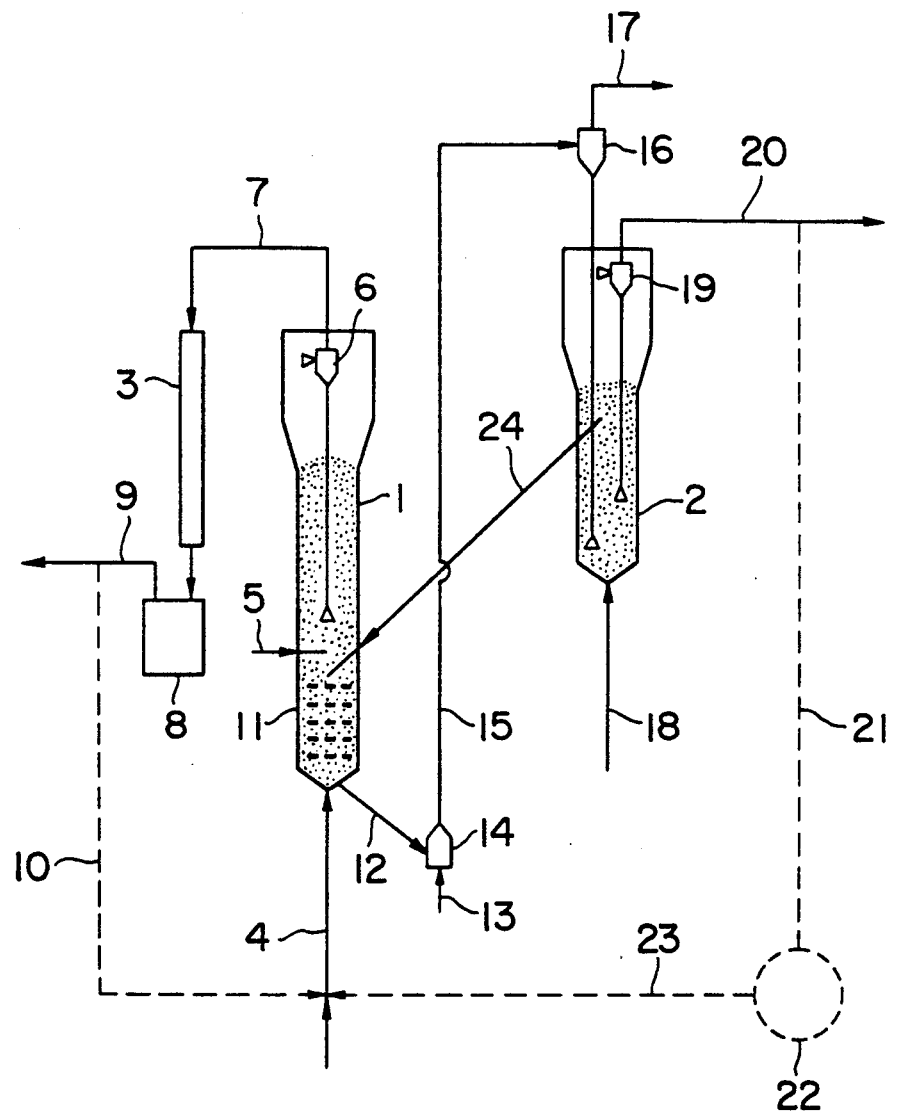

HYDRODEALKYLATION PROCESS

BACKGROUND OF THE INVENTION

1. Field of the art

This invention relates to a process in which feed oils comprising alkylaromatic compounds are continuously hydrodealkylated by means of fluidized beds of particles which have hydrodealkylation activity.

2. Related art

Among the techniques heretofore known of catalytic hydrodealkylation of feed oils comprising alkylaromatic compounds, there are the processes which use chromiaalumina or cobalt-molybdenum oxide-containing particles or others as the catalyst.

Hydrodealkylation of alkylaromatic compounds is an exothermic reaction with more than about 10 kcal/mol for each methyl group when the alkyl is methyl. Generally, feed oils to be subjected to hydrodealkylation often contain polyalkylaromatic compounds and naphthenic or paraffinic hydrocarbons, and in such cases, hydrodealkylation of 2 to 5 mols of methyl groups per mol of feed oil, i.e., exothermic reaction of about 20 to 50 kcal/mol or more, occurs. In the prior art of hydrodealkylation, this large amount of heat generated by the reaction causes a wide temperature distribution and difficulty of temperature control in the reactor due to the nature of fixed bed reactor employed in the known process as described, for example, in Japanese Patent Publication No. 3024/64 and Japanese Patent Application Laid-Open Specification No. 13735/84. As a result, various problems tend to occur such as reduction of selectivity and generation of a large amount of tar or coke due to side reactions, deactivation of catalyst and plugging of the reactor.

In order to minimize these problems, such methods are tried or employed that, for example, the fixed bed reactor is made to have multi-stage structure and a large amount of cooling gas is introduced into the several parts in the reactor to reduce the temperature distribution, and/or feed oil is pre-treated and the reaction is conducted under a high hydrogen pressure higher than about 30 kg/cm$^2$ to suppress the side reactions. However, any of these methods is not satisfactory to solve the problems because the effects are insufficient and the methods are not economical due to the sophisticated reactor structure and troublesome operation. Furthermore, operation of these processes must be frequently interrupted by decoking operation or catalyst replacement in a relatively short interval.

In U.S. Pat. Nos. 2,780,661 and 2,924,569, a process utilizing a fluidized bed as the reactor to reduce the temperature distribution in the reactor and to enable low temperature feed is described. However, these relate to a thermal hydrodealkylation process in which substantially inert particles such as sand or silica are used, but do not relate to the catalytic process described in this invention. Although those patents describe that the particles of 100 to 400 mesh in size should be used as fluidized particles, but to the best of our knowledge good fluidized state and homogenization of temperature throughout the reactor would not be attained with these particles. According to S. R. Beghea, R. L. Heinlich, A. B. Souby and L. T. Yule: Ind. Eng. Chem., 50, 1245 (1958) in which results of a pilot plant operation based on this method are described in detail, it is described that only poor fluidized state, i.e., severe slugging, was observed, and a large temperature distribution still remained in the reactor bed. Furthermore, this process is based on the same concept as that in the fixed bed processes that coke formation should be limited at as low a level as possible, and, therefore, a high pressure at 28 to 70 kg/cm$^2$, preferably at about 42 kg/cm$^2$ as well as a high concentration of hydrogen are necessary.

Such a high pressure, though it is effective to suppress or limit the coke formation, is much too high to be in the range in which the rate of hydrodealkylation as the main reaction is effectively promoted by the pressure, and brings about such inadvantage us aspects that it causes the unnecessary increase of the power consumption of compressors and the cost of reactor materials and, in the catalytic hydrodealkylation process, promotes undesirable hydrocracking of aromatic rings and lowers the selectivity of dealkylated products.

This invention proposes a new catalytic hydrodealkylation process in which high selectivity and activity can be maintained at relatively low hydrogen pressure, and the problems in the processes of the prior art mentioned above are solved.

SUMMARY OF THE INVENTION

According to one aspect of the present invention, there is provided a process for catalytic hydrodealkylation of a feed oil comprising an alkylaromatic wherein a two-column apparatus, one column for the catalytic hydrodealkylation and the other column for regeneration of the catalyst, is used, which comprises conducting the hydrodealkylation of a feed oil in the presence in a first column of a fluidized bed of a catalyst comprising substantially spherical particles having activity of hydrodealkylation of an alkylaromatic of a weight mean diameter of 25 to 250 μm, an apparent density of 0.3 to 1.5 g/cm$^3$, a pore volume of 0.10 to 1.5 cm$^3$/g under the conditions maintained for the hydrodealkylation in the column of a total pressure of 2 to 30 kg/cm$^2$, a hydrogen partial pressure of 1.5 to 20 kg/cm$^2$ and a temperature of 350° to 700° C.; continuously withdrawing the particles having coke deposited thereon from the column for the hydrodealkylation and transferring the particles to a second column wherein the particles, while they are in a fluidized bed, are treated with a gas comprising molecular oxygen to burn or gasify the coke thereby to regenerate the particles; and recycling the regenerated particles to the first column.

According to another aspect of the present invention is a process for hydrodealkylation of a feed oil comprising an alkylaromatic which comprises contacting in the presence of hydrogen a feed oil comprising an alkylaromatic with a catalyst comprising vanadium carried on alumina particles in a quantity calculated as metal of no higher than 30% by weight.

According to this invention, by utilizing circulating fluidized beds, using catalyst particles with specified properties as fine-particle fluidized beds, and conducting the hydrodealkylation reaction in the fluidized bed reactor under relatively low hydrogen pressure, remarkable effects are realized as follows. Effects on the reaction:

(1) By using catalyst particles with the specified properties, the effect of homogenizing temperature in the reactor is remarkably enhanced, and it is made possible to conduct the highly exothermic hydrodealkylation reaction at the optimum temperature, whereby selectivity reduction at higher temperature or lack of reactivity at lower temperature is prevented, and the desired dealkylated products can be obtained at a high yield.

(2) By conducting the reaction under relatively low hydrogen pressure, hydrocracking of aromatic rings by the reactivity of catalyst is prevented to a minimum degree, so that the hydrodealkylation reaction is selectively proceeded to enhance the yield of the desired dealkylated products, and reduction of construction cost of the process, compression cost, and hydrogen consumption is made possible, by which the process economy is improved.

(3) Continuous regeneration of the catalyst particles with the circulating fluidized bed process consisting of two beds in a two-column apparatus, i.e., reactor and regenerator, prevents the accumulation of coke on the catalyst particles and accompanying deactivation of the catalyst, which have been almost inevitable in the heretofore known processes, and makes it possible to maintain the high activity and selectivity which the catalyst originally possesses, and to conduct the continuous operation of the process.

(4) In the fine-particle fluidized bed reactor with a good fluidized state, gaseous reactants contact the catalyst in a piston flow manner, in which shortcut or by-passing of unconverted reactants is prevented, and contact efficiency between the reactant gas and the catalyst particles is high. As a result, a high conversion of the hydrodealkylation reaction can be attained in the single reactor. Effects on the processing:

(5) Since coke formation does not lead to any severe problem in the present invention, unlike in the other known processes, it is made possible to use feed oils containing easily coke-forming materials such as high boiling point compounds, dienes and olefins, for example, catalytic cracking cycle oil, coal tar, and others, which would be difficult or impossible to use in the known processes, and pre-treating of feed oils which requires large costs can be avoided or simplified.

(6) Due to the occlusion effect of micropores of the particles, bogging of the bed which heavy fractions in the feed oil and polycondensed materials cause to occur, i.e. a defluidized state due to sticking together of the particles by liquid materials, can be prevented, and liquid feed at a low temperature is made possible.

(7) Coke deposited on the particles in the reactor can be continuously and efficiently gasified or burnt in the regenerator, and produced gas in the regenerator can be utilized as synthesis gas or fuel gas, and/or as heat source. As deposited coke on the particles is factually kept in the micropores in the particles, there is no discharging of mass of coke in the regenerator due to separation from the particles, and therefore gasification efficiency is high.

(8) It is made possible to markedly lower the temperature of the feed oils compared with those in any known process because of heat supply with the circulating particles from the regenerator at a high temperature to the reactor, which provides such economic merits that pre-heating furnace or heat-exchanger of the feed can be omitted or simplified, and serves to prevent coking trouble in the pre-heating of the feed.

(9) Due to the fine-particle fluidized bed with good fluidized state, operation of the process is easy and simple, and erosion of the reactor materials is negligible.

BRIEF DESCRIPTION OF DRAWINGS

The FIG. shows an example of a flowsheet of a process for conducting hydrodealkylation according to the present invention.

DETAILED DESCRIPTION OF THE INVENTION IN PREFERRED EMBODIMENT

Feed oils and products

There is no limitation to feed oils, if they are mono- or poly-aromatic hydrocarbons or hetero-ring containing compounds which possess alkyl substituent such as toluene, xylene, methylnaphthalene, and others, or oils which contain any of them such as, for example, catalytic cracking cycle oil, heavy reformate, oils from naphtha cracker, oils from coal liquefaction, coal tar, and others.

Reaction products are cracked oil, cracked gas and regeneration gas. The regeneration gas can be flue gas or synthesis gas, depending on regeneration condition. The cracked oil mainly contains partially or fully dealkylated products of the compounds included in the feed oil, such as benzene, toluene, naphthalene, and others. The cracked gas is mainly composed of saturated hydrocarbon gas, such as methane, ethane and others. These cracked products are discharged with fluidizing gas containing hydrogen from the reactor, and can be separated into the cracked oil and the cracked gas to be recovered separately by cooling with known technique.

Catalyst particles

The particles which are used in the process of this invention must be those which have catalytic activity of hydrodealkylation. As such catalyst particles, there are many known particles, such as chromia-alumina particles, particles supporting or carrying cobalt oxide, molybdenum oxide, Ni, Rh, Pt, and others, silica-alumina particles and other particles. Silica particles and alumina particles are preferable as the catalyst carrier. Silica-alumina- is one of effective catalysts in the present invention and a wording "silica-alumina" herein indicates a crystalline or amorphous aluminosilicate having a remarkable acidity of a ratio of $SiO_2:Al_2O_3$ of ca. 70:30 to ca. 90:10.

The properties of the particles which are used in the process of this invention are: the weight mean diameter being 25 to 250 82 m, preferably 40 to 120 µm, the apparent bed density being 0.3 to 1.5 g/cm$^3$, preferably 0.4 to 1.3 g/cm$^3$, and the shape being substantially spherical. Fluidized beds with such particles are called fine-particle fluidized beds, in which the size of bubbles generated in the bed is small, pressure fluctuation is small, and the fluidized state is quite smooth, compared with fluidized beds with coarse particles which have larger size and/or larger density. In these fine-particle fluidized beds, catalyst particles are effectively contacted with gas to promote the reaction, operation of the reaction is easy, and erosion of the particles and the reactor materials is very small (Miyauchi et al.: Advances in Chem. Eng., Vol. 11, p. 275–448).

Furthermore, the particles used in the process of this invention are the porous particles with the pore volume of 0.1 to 1.5 cm$^3$/g, preferably 0.2 to 1.2 cm$^3$/g. Such porous particles quickly occlude the liquid material, i.e. feed oil and polycondensed substance, in the micropore, into being less adhesive with each other, and thus keep the bed in a good fluidized state to promote the dealkylation reaction in the bed. This effect also enables to introduce the feed oil in the liquid state into the reactor, and prevents the fluidized particles from sticking together due to the heavy fraction of high boiling point included in the feed oil or polycondensed substance produced by a side reaction with the dealkylation. On account of this effect, deposited coke is kept in the micropore of the particles, and therefore the gasification can be carried out perfectly.

The aforementioned properties of the particles should be stably maintained at the reaction temperature.

The particles suitably used in the process of this invention can be manufactured, for example, in the way that properly selected, aforementioned active substance for hydrodealkylation is supported by impregnation, for example, on alumina-predominant particles or silica-predominant particles which can be manufactured by spray drying method and are conventionally used as support for the catalyst for fluidized beds.

Reaction process

The fine-particle fluidized bed reactor for the hydrodealkylation is equipped with the inlet of fluidizing gas comprising hydrogen in the lower part, the inlet of feed oil in the intermediate part, and the cyclone system to recover entrained particles and the outlet of reaction products which is connected with the cyclone system in the upper part. The reactor is also equipped with the inlet of the circulating particles from the regeneration step and the outlet of the circulating particles to the regeneration step.

One of the important features of the process described in this invention is to keep the total pressure at a level between 2 and 30 kg/cm$^2$, preferably between 3 and 20 kg/cm$^2$, the hydrogen partial pressure at a level between 1.5 and 20 kg/cm$^2$, preferably between 3 and 15 kg/cm$^2$ in the reactor. Even under a relatively low hydrogen pressure like this, high activity and selectivity can be realized in the process according to this invention by conducting continuous regeneration of the catalyst which makes it possible to keep the coke level of the catalyst particles low. The gas for fluidization comprises as its major component hydrogen, i.e. at least 50 mole %, preferably 50 to 100 mole % of hydrogen.

According to this invention, the ratio of the circulating particles rate to the feed oil rate is usually 0.1 to 10, preferably 0.2 to 5 as weight ratio. The coke level of the catalyst particles depends on this ratio when the reaction and regeneration conditions are kept in the stable states. The amount of the coke on the catalyst particles in the reactor is usually not more than 15 wt%, preferably not more than 10 wt%, further preferably not more than 5 wt% of the whole weight of the particle. According to this invention, the reaction temperature is 350° to 700° C., preferably 400° to 650° C., the superficial velocity of the fluidizing gas is 0.05 to 2 m/sec, preferably 0.1 to 1 m/sec, and the apparent contact time (height of fluidized bed/superficial gas velocity) is 3 to 120 sec, preferably 6 to 60 sec.

Regeneration process

The fine-particle fluidized bed reactor for the catalyst regeneration is equipped with the inlet of molecular oxygen-containing gas to burn or gasify the deposited coke on the catalyst particles in the lower part, and the cyclone system to recover entrained particles and the outlet of the flue gas or gasification product gas which is connected with the cyclone system in the upper part.

The oxygen-containing gas is usually air for the burning or air and steam; molecular oxygen and steam; air or molecular oxygen and nitrogen; or others for the gasification of the coke, but is not limited to them. Usually, the temperature for the burning is 600° to 900° C., preferably 650° to 850° C., and the temperature for the gasification is 750° to 1000° C., preferably 800° to 950° C. It is desirable that the total pressure in the regenerator is about the same as that in the reactor.

In order to completely remove the coke deposited during the reaction, it is necessary to give enough residence time to the particles in the regeneration step. In the case of burning the coke, the residence time between several seconds and several ten minutes is enough, while the residence time between several minutes and several hours is necessary in the case of gasifying the coke. When burning the coke, the superficial gas velocity is 0.05 to 20 m/sec, preferably 0.1 to 10 m/sec. When the velocity exceeds about 3 m/sec, the density of the particles is small (dilute fluidized bed) compared with that in the usual dense fluidized bed. When gasifying the coke, the superficial gas velocity is 0.05 to 2 m/sec, preferably 0.1 to 1 m/sec.

Flowsheet

The FIG. shows an example of flowsheet as the embodiment of the hydrodealkylation according to this invention.

In the FIG., 1 denotes the fine-particle fluidized bed reactor for hydrodealkylation of feed oil, 2 denotes the fine-particle fluidized bed regenerator for removing the deposited coke and regenerating the catalysts, and 3 denotes a cooling unit for separating the reaction products into liquid products and cracked gas by cooling.

Hydrogen or hydrogen-containing gas is introduced from line 4 into the lower part of the reactor 1, feed oil is introduced from line 5 into the intermediate part of the reactor, and the catalyst particles are fluidized. After removing entrained catalyst particles by the cyclone 6 in the upper part of the reactor, reaction products flow through line 7 to the cooling unit 3, where product oil is separated and held in a receiver 8, and cracked gas is purged out through line 9. In the preferable embodiment, part of the cracked gas is returned to line 4 through line 10.

The catalyst particles in the reactor flow down through multi-stage perforated plates 11 equipped in the lower part of the reactor, in which the remaining heavy oil fraction in the micro-pores of the particles is stripped, and the catalyst particles with deposited coke flow out of the reactor through line 12, then ascend in transport line 15 by N$_z$ gas introduced from line 13 through ejector 14 to cyclone 16, in which the particles are separated to be introduced into the regenerator and the N$_2$ gas is discharged through line 17.

From line 18 oxygen-containing gas which is the mixture of air, molecular oxygen, steam and other gas or any of them is introduced into the lower part of the regenerator 2, in which the catalyst particles containing deposited coke are fluidized, and the coke is burnt or gasified. The flue gas or gasification product gas is discharged through line 20 after removing entrained particles in the cyclone 19 in the upper part of the regenerator. The catalyst particles, which are thus regenerated by removing the deposited coke, are returned to the reactor through an overflow line 24.

Part of the gasification product gas may be introduced through line 21 into a gas-treating unit 22, which comprises, for example, steps of conversion of CO to H$_2$, water removal, purification and others, and be returned to line 4 through line 23.

More preferred embodiment

One of the preferred embodiments of the present invention is such that the catalyst particles are alumina particles carrying a vanadium oxide in a quantity calculated as metal of no higher than 30%. Preferably, the alumina particles meet the requirement for the particles for hydrodealkylation as shown herein above, hydrodealkylation is conducted as shown herein above, and regeneration of the catalyst particles is conducted under the condition shown herein above, although hydrodealkylation by means of the catalyst does not require the regeneration step (if so desired).

The hydrodealkylation by means of the V$_m$O$_n$-Al$_2$O$_3$ catalyst can be defined as a process for hydrodealkylation of a feed oil comprising an alkylaromatic which comprises contacting in the presence of hydrogen a feed oil comprising an alkylaromatic with a catalyst comprising a vanadium oxide carried on alumina particles in a quantity calculated as metal of no higher than 30% by weight, which process can be practiced, when so desired, in a two-column apparatus as shown herein above, wherein all the particulars shown herein above including those on the flowsheet and on the catalyst carrier will apply.

Vanadium is carried as an oxide (V$_m$O$_n$) on the alumina particles by any convenient method. One of such a convenient methods is to use as a vanadium source easily decomposable and solvent (preferably water)-soluble vanadium compounds such as vanadates including metavanadate such as, e.g. ammonium metavanadate, soluble in aqueous oxalic acid, or acetylacetone vanadium soluble in toluene, in such a way that alumina particles are impregnated with the solution, the alumina particles are then dried and heated to decompose the vanadium compound carried on them into the oxide which may be e.g. V$_2$O$_5$, which will preferably be hydrogenated into a reduced form of a lower oxidation degree, such as, e.g. V$_2$O$_3$ and/or V$_2$O$_4$, before being used in hydrodealkylation or during hydrodealkylation.

Example 1

Apparatus

An experimental apparatus as shown in FIG. constructed with a stainless-steel sheet and pipe was used. The reactor was a cylinder having a section for housing a fluidized bed of an inner diameter of 8 cm and a height of ca. 2.5 m with an inlet for a feed oil at ca. 0.5 m above from the bottom, the section above the inlet for a feed oil being a reaction zone and the section below the inlet being a stripping zone. 5 perforated plates having an opening of ca. 30% of the horizontal cross-section of the fluidized bed are placed within the stripping zone with 8 cm intervals. A regeneration apparatus was made of a cylinder having a section for housing a fluidized bed of an inner diameter of 8 cm and a height of ca. 3 m.

Experiment conditions

A catalyst comprising 7.0% by weight of Ni as an active component carried on porous alumina particles was charged in the reactor in a quantity of ca. 5 kg and in the regeneration apparatus in a quantity of ca. 6 kg.

6.8 Nm$^3$/h of H$_2$ gas at room temperature was introduced into the reactor via an inlet at the bottom and 3.6 kg/h of a feed oil heated at ca. 150° C. was sprayed into the reactor via the inlet for a feed oil. From the bottom were continuously withdrawn 3.2 kg/h of the catalyst particles having coke deposited thereon, and were sent to the regeneration apparatus by means of N$_2$ gas. Via an inlet at the bottom of the regeneration apparatus were introduced N$_2$ initially and then air at room temperature in a quantity of 5.3 Nm$^3$/h when the reaction got stationary.

The temperatures of the fluidized beds in the reactor and in the regeneration apparatus were maintained at 580° C. and 850° C., respectively, by heating and/or cooling from outside, and the total pressure was maintained at a constant level of 8.0 kg/cm$^2$ by a pressure regulating means.

Within the reactor and the regeneration apparatus, the superficial gas velocities were both ca. 15 cm/sec, and the residence times of the catalyst particles were ca. 1.6 h and ca. 1.9 h. The ratio of the quantity of the particles recycled/the quantity of oil fed was ca. 0.9 kg/kg.

The reaction product was cooled by means of water and brine, and was separated into liquid products and cracked gas.

The catalyst used was made up of substantially spherical particles having the following characteristics.

| Weight mean diameter: | 68 μm |
|---|---|
| Apparent bed density: | 0.52 g/cm$^3$ |
| Pore volume: | 0.79 cm$^3$/g |

As a feed oil was used commercial β-methyl-naphthalene (purity: 96.9% by weight). Results obtained:

The results obtained for the run for 1 h after a steady state had substantially been reached which, in turn, was reached ca. more than 5 hrs. after the start of a feed oil are as follows.

| (1) Liquid product obtained: | 0.947 kg/kg |
|---|---|
| naphthalene | 33.3 wt. % |
| β-methylnaphthalene | 45.9 wt. % |
| α-methylnaphthalene | 18.7 wt. % |
| dimethylnaphthalene | 1.9 wt. % |
| others | 0.2 wt. % |
| total | 100.0 wt. % |
| (2) Cracked gas obtained* | 0.067 Nm$^3$/kg |
| methane | 97.4 vol % |
| ethane and others | 2.6 vol % |
| total | 100.0 vol % |
| (3) Gasification product gas obtained (dry) | 1.5 Nm$^3$/kg |
| N$_2$ | 79.1 vol % |
| O$_2$ | 19.7 vol % |
| CO$_2$ and others | 1.2 vol % |
| total | 100.0 vol % |
| (4) Other data involved: | |
| Coke on the particles in the reactor | 1.5 wt. % |
| Coke on the particles in the regeneration apparatus | 0.3 wt. % |

*H$_2$ for fluidizing is not included

EXAMPLE 2

Apparatus

The same apparatus as used in Example 1 was used.

Experiment conditions

The same catalyst as used in Example 1 was charged in the reactor and the regeneration apparatus in quantities of ca. 5 kg and ca. 6 kg, respectively. From the bottom of the reactor was introduced 6.8 Nm$^3$/h of H$_2$ gas at room temperature and from the inlet for a feed oil was sprayed into the reactor 3.6 kg/h of a feed oil heated at ca. 250° C. From the bottom of the reactor was continuously withdrawn 20 kg/h of catalyst particles having coke deposited thereon, and were sent to the regeneration apparatus by means of $N_2$ gas. From the bottom of the regeneration apparatus was introduced $N_2$ gas and then molecular oxygen at room temperature and steam heated at ca. 400° C., in quantities of 0.63 $Nm^3$/h and 3.8 kg/h, respectively, when steady state in the reaction was reached.

The temperatures of the fluidized beds in the reactor and the regeneration apparatus were maintained at 630° C. and 900° C., respectively, by heating and/or cooling from outside, and the total pressure was maintained at a constant level of 8.0 kg/cm$^2$ by a pressure regulating means. Within the reactor and the regeneration apparatus, the superficial gas velocities were ca. 15 cm/sec and ca. 20 cm/sec, and the residence time of the particles were ca. 15 min. and ca. 18 min., respectively.

The reaction product was cooled by means of water and brine, and was separated into liquid products and cracked gas.

As a feed oil was used crude coal tar of a specific gravity of 1.12 and the Conradson carbon (CCR) of 24.7% by weight.

| Feed oil composition: | |
| --- | --- |
| naphthalene | 12.4 wt % |
| benzene, toluene, xylenes | 0.9 wt % |
| biphenyl | 0.6 wt % |
| others | 86.1 wt % |
| total | 100.0 wt % |

Results obtained

The results obtained for the run for 1 hour after a steady state had substantially be reached which, in turn, was reached ca. more than 5 h after the start of a feed oil are as follows.

| (1) Liquid product obtained: | 0.623 kg/kg |
| --- | --- |
| naphthalene | 27.9 wt % |
| benzene, toluene, xylenes | 2.7 wt % |
| biphenyl | 3.5 wt % |
| others | 65.9 wt % |
| total | 100.0 wt % |
| (2) Cracked gas obtained* | 0.085 $Nm^3$/kg |
| methane | 74.1 vol % |
| ethane and others | 25.9 vol % |
| total | 100.0 vol % |
| (3) Gasification (burning) gas obtained (dry) | 1.1 $Nm^3$/kg |
| $CO_2$ | 24.9 vol % |
| CO | 22.6 vol % |
| $H_2$ | 51.4 vol % |
| $CH_4$ and others | 1.1 vol % |
| total | 100.0 vol % |
| (4) Other data involved | |
| Coke on the particles in the reactor | 9.2 wt. % |
| Coke on the particles in the regeneration apparatus | 3.7 wt. % |
| Naphthalene in the product | 1.40 kg/kg |
| Naphthalene in the feed | |

In this run, the increments in naphthalane and benzene, toluene and xylene are assumed to have been produced by the hydrodealkylation of alkylnaphthalenes and higher alkylbenzenes contained in the feed oil used.

EXAMPLE 3 AND COMPARATIVE EXAMPLE 3

The same catalyst as used in Example 1 was used in Example 3 and Comparative Example 3 (A and B), and the two-column fluidized bed apparatus was used in Example 3 but a fixed bed reactor was used in Reference Example 3 wherein the catalyst was charged in a reactor tube of 2.8 cm diameter in ca. 12 cm length. Continuous hydrodealkylation for 48 hrs. under the conditions used in Example 1 was conducted in these Examples, wherein the same hydrogen partial pressures were used in Example 3 and Comparative Example 3A but Comparative Example 3B was run under a partial hydrogen pressure which was ca. twice that used in Example 3. As the feed oil was used a catalytic cracking cycle oil containing 45.9% by weight of methyl-, dimethyl and trimethylnaphthalene as an alkylnaphthalene.

In Comparative Example 3 wherein a fixed catalyst bed was used, a mixture of a feed oil and hydrogen preheated was introduced to the catalyst bed from its top, and the product leaving from the bottom of the catalyst bed was cooled by means of water and brine and separated into a liquid product and cracked gas. The temperature at the middle of the catalyst bed was considered to be a reaction temperature and was maintained at a constant level.

In Example 3 wherein a fluidized bed reactor was used, the regeneration apparatus was operated with air at room temperature for regeneration of the catalyst.

In Table 1 are set forth the conversion of the alkylnaphthalene and the selectivity to naphthalene. In the fixed catalyst bed, a temperature distribution was found which was much broader than that found in the fluidized catalyst bed and the catalyst activity and the selectivity were gradually lowered due to coke formation and deposition on the catalyst. This tendency was remarkable in Comparative Example 3A wherein the hydrogen partial pressure was the same as that in Example 3. In Comparative Example 3B, the higher hydrogen partial pressure used was in favor of reduction in coke deposition and catalyst degradation but the reduction was not satisfactory, and entailed reduction in the selectivity due to hydrocracking of aromatic rings of a side reaction accelerated. Operation under such a high pressure may also be less economical.

The fluidized bed operation according to the present invention succeeded in hydrodealkylation under lower hydrogen partial pressure with higher conversion and selectivity in comparison with the conventional fixed bed operation.

TABLE 1

| | Example 3 | Comparative Example 3 | |
| --- | --- | --- | --- |
| | | A | B |
| Reactor | 2-col. fluidized | fixed bed | fixed bed |
| Reaction temp., °C. | 580 | 580 | 580 |
| $H_2$ partial press., kg/cm$^2$ | 18 | 18 | 35 |
| Contact time, sec | 15.1 | 15.4 | 15.1 |
| Conversion of alkylnaphthalene, mole % | 65.9 | 48.2 | 65.1 |
| Selectivity to naphthalene, mole % | 88.1 | 87.6 | 82.4 |

EXAMPLE 4 AND COMPARATIVE EXAMPLE 4

Apparatus

The same apparatus as used in Examples 1 and 2.

Experiment conditions

The catalyst used comprised ca. 12 wt% of Ni as an active component carried on alumina particles shown in Table 2. The same crude coal tar as used in Example 2 was used as a feed oil. The experiment conditions used were the same as used in Example 2, and the volume of the catalyst was substantially the same as in Example 2.

Results obtained

As shown in Table 2, uses of catalyst particles A and B which meet the requirements according to the present invention resulted in very good fluidization, in sharp temperature distribution in the fluidized bed and in smooth progress of hydrodealkylation and of catalyst regeneration. As the result, the high levels of activity and selectivity of the catalyst were maintained.

To the contrary, uses of the particles C of a higher apparent density and of the particles D of a larger weight mean diameter and a higher apparent density resulted in poor fluidization due to occurrence of slugging in the fluidized bed, in generation of broader temperature distribution, and in lowering of the catalyst activity. Use of the particles E of a smaller pore volume resulted in very poor fluidization due to occurrence of bogging in the fluidized bed ca. 10 minutes after the start of experiment whereby continuation of operation was impossible.

It was thus shown that use of catalyst particles which do not meet the requirement in accordance with the present invention fails to carry out hydrodealkylation with a high activity and a high selectivity.

TABLE 2

| Particles | Example 4 | | Comparative Example 4 | | |
|---|---|---|---|---|---|
| | A | B | C | D | E |
| Weight mean diameter, $\mu m$ | 70 | 170 | 170 | 340 | 110 |
| Apparent density, $g/cm^3$ | 0.81 | 1.28 | 1.61 | 1.61 | 1.87 |
| Pore volume, $cm^3/g$ | 0.45 | 0.21 | 0.12 | 0.12 | 0.06 |
| Fluidization | good | good | poor slugging | poor slugging | poor bogging[*1] |
| Temperature distribution[*2] °C. | 4 | 6 | 21 | 28 | $\geq 40$ |
| Conversion, wt % | 87.3 | 85.1 | 69.4 | 66.0 | — |
| Selectivity, mole % | 86.9 | 86.8 | 81.0 | 79.1 | — |

[*1]Reaction was stopped 10 minutes after the start.
[*2]The temperature difference between the highest and the lowest detected in the fluidized bed

EXAMPLE 5

Vanadium was carried on 4 liters of alumina particles of a pore volume of 0.96 $cm^3/g$, specific surface of 240 $m^2/g$, a weight mean diameter of 70 $\mu m$ and an apparent density of 0.45/$cm^3$, the particles being substantially spherical according to the following procedure.

80 g of oxalic acid was dissolved in 1520 g of water, and 39 g of ammonium metavanadate was then dissolved in the solution. The alumina particles were then impregnated with the solution thus produced, and were dried in air at 105° C. for 1 h. These particles were charged in a fluidized bed reactor of an inner diameter of 8 cm, and were heated at 250° C. for 1 h with introduction of air thereby to decompose the ammonium metavanadate, and then subjected to reduction treatment with hydrogen at 450° C. for 3 h and at 600° C. for 1 h, whereby a catalyst comprising 0.9% by weight as a metal of vanadium was obtained.

Similarly, catalysts comprising 0.3% by weight, 7.8% by weight and 25.8% by weight, all calculated as a metal, of vanadium were respectively produced.

Hydrodealkylation of $\beta$-methylnaphthalene was conducted in the fluidized bed reactor referred to above wherein the catalysts referred to above and alumina particles referred to above with no vanadium carried thereon were respectively used, under the conditions of a temperature of 600° C., a hydrogen partial pressure of ca. 7.8 $kg/cm^2$, a contact time of ca. 8 seconds, and a feed rate of the $\beta$-methylnaphthalene of ca. 1.2 kg/h.

The results obtained are set forth in Table 3. Hydrodealkylation was thus conducted successfully in a high yield and in a high selectivity according to the present invention.

Similar hydrodealkylation was conducted wherein a catalyst which was the same as those used in the runs referred to above except for the content of vanadium being 38% by weight was used. The fluidization was poor, and the naphthalene yield and selectivity were low.

TABLE 3

| | Example | | | | Comp. Ex. | |
|---|---|---|---|---|---|---|
| V content, wt % | 0.3 | 0.9 | 7.8 | 25.8 | 0 | 38 |
| Naphthalene yield, mole % | 26.5 | 37.2 | 43.2 | 39.0 | 18.6 | 25.9 |
| Naphthalene selectivity, mole % | 93.6 | 93.5 | 94.7 | 95.8 | 93.5 | 91.7 |

Example 6

Uses were made of a catalyst comprising 7.3% by weight of vanadium produced according to the procedure set forth in Example 5 and of a catalyst comprising 7.2% by weight of nickel carried on alumina particles as used in Example 5 in hydrodealkylation of $\beta$-methylnaphthalene in an apparatus as used in Example 5. Nickel has been known to have hydrodealkylation activity.

The reaction conditions used were a temperature of 600° C., a hydrogen partial pressure of ca. 8.0 $kg/cm^2$, a contact time of ca. 8 seconds, and a feed rate of $\beta$-methylnaphthalene was ca. 1.2 kg/h.

The results obtained are set forth in Table 4. Hydrodealkylation was thus conducted successfully in a high yield and in a high selectivity.

TABLE 4

| | Example | Reference |
|---|---|---|
| Metal content, wt % | V: 7.3 | Ni: 7.2 |
| Naphthalene yield, mole % | 43.8 | 35.9 |
| Naphthalene selectivity, mole % | 94.7 | 92.7 |

EXAMPLE 7

The apparatus as used in Example 5 was modified so that a fluidized bed regeneration apparatus of an inner diameter of 2.8 cm was combined, between the fluidized bed of which catalyst particles were recycled.

Use was made of 4.5 liters of a catalyst comprising 2.8% by weight of vanadium produced as in Example 5.

To the apparatus were introduced ca. 2.4 Nm³/h of hydrogen and ca. 1.2 kg/h of a feed oil which was a catalytic cracking cycle oil to conduct hydrodealkylation under the conditions of a temperature of 600° C., a hydrogen partial pressure of ca. 7.5 kg/cm³, and a contact time of ca. 15 seconds. To the regeneration apparatus were introduced ca. 0.55 Nm³/h of air diluted with nitrogen into an oxygen concentration of ca. 4 volume % and ca. 130 g/h or steam to conduct regeneration of the catalyst having coke deposited thereon under the same pressure as in the reactor at 740° C.

In Tables 5 and 6 are set forth the compositions of the feed oil used and the liquid product produced.

Hydrodealkylation of a feed oil containing sulfur and nitrogen compounds was successfully conducted according to the present invention.

TABLE 5

| Composition of the catalytic cracking cycle oil, wt % | |
|---|---|
| Naphthalene | 6.4 |
| Methylnaphthalene | 14.5 |
| Dimethylnaphthalene | 24.4 |
| Trimethylnaphthalene | 6.9 |
| C₄ Benzenes, indenes and others | 47.8 |
| Total | 100.0 |
| S-content | 0.2 wt % |
| N-content | 210 ppm by wt. |

TABLE 6

| Composition of the liquid product produced, wt % | |
|---|---|
| Naphthalene | 67.4 |
| Methylnaphthalenes | 8.9 |
| Dimethylnaphthalenes | 0.8 |
| Trimethylnaphthalenes | 0.6 |
| Benzene, toluene, xylenes | 17.0 |
| C₄⁺ benzenes, indenes | 3.9 |
| Others | 1.4 |
| Total | 100.0 |

What is claimed is:

1. A process for catalytic hydrodealkylation of a feed oil in a two-column apparatus, comprising:
    conducting the hydrodealkylation of said feed oil in a first column under a total pressure 2 to 30 kg/cm², a hydrogen partial pressure of 1.5 to 20 kg/cm² and a temperature of 350° to 700° C. in the presence of a fluidized bed of a catalyst, said feed oil comprising an alkylaromatic, and said catalyst being supported or unsupported, wherein said catalyst comprises substantially spherical particles having a weight mean diameter of 25 to 250 μm, an apparent density of 0.3 to 1.5 g/cm³, and a pore volume of 0.10 to 1.5 cm³/g, said unsupported catalyst being selected from the group consisting of chromia-alumina and silica-alumina, and said supported catalyst comprising:
    (i) support particles, and
    (ii) an active substance selected from the group consisting of cobalt oxide, molybdenum oxide, nickel, rhodium, platinum, vanadium oxide and chromium oxide, said active substance being supported on said support particles;
    continuously withdrawing the catalyst having coke deposited thereon from the first column;
    transferring the catalyst to a second column;
    regenerating the catalyst in the second column by treating said catalyst with a gas comprising molecular oxygen to burn or gasify the coke; and
    recycling the regenerated catalyst to the first column.

2. The process as claimed in claim 1, wherein the fluidized bed of the catalyst is maintained in the first column by means of a gas the major component of which is hydrogen.

3. The process as claimed in claim 1, wherein the hydrogen partial pressure is 3 to 15 kg/cm³.

4. The process as claimed in claim 1, wherein the hydrodealkylation is conducted under the conditions of superficial gas velocity of 0.05 to 2 m/sec and an apparent contact time defined by height of fluidized bed/superficial gas velocity of 3 to 120 seconds.

5. The process as claimed in claim 1, wherein the gas for regeneration comprising molecular oxygen is selected from the group consisting of air and mixtures of air or molecular oxygen and a diluent selected from the group consisting of nitrogen and steam.

6. The process as claimed in claim 1, wherein the regeneration is conducted under the conditions of a temperature of 600° to 900° C. when the regeneration is based on burning of the coke or 750° to 1000° C. when the regeneration is based on gasification of the coke, a total pressure which is substantially the same as that maintained in the hydrodealkylation, step a residence time sufficient enough for burning or gasification of the coke, and a superficial gas velocity of 0.05 to 20 m/sec when the regeneration is based on burning of the coke or 0.05 to 2 m/sec when the regeneration is based on gasification of the coke.

7. The process as claimed in claim 1, wherein said catalyst is a vanadium oxide supported on alumina particles wherein the vanadium of said vanadium oxide is present in a quantity of no higher than 30% by weight of the total of the alumina particles and the vanadium oxide.

8. A process for hydrodealkylation of a feed oil comprising an alkylaromatic which comprises contacting in the presence of hydrogen a feed oil comprising an alkylaromatic with a catalyst comprising a vanadium oxide supported on alumina particles, wherein the vanadium of said vanadium oxide is in a lower oxidation state than V₂O₅ and is present in a quantity of no higher than 30% by weight of the total of the alumina particles and the vanadium oxide.

9. The process as claimed in claim 8, wherein said hydrodealkylation is conducted in a first column under a total pressure of 2 to 30 kg/cm², a hydrogen partial pressure of 1.5 to 20 kg/cm² and a temperature of 350° to 700° C. in the presence of a fluidized bed of a catalyst, said feed oil comprising an alkylaromatic, and said catalyst comprising substantially spherical particles having a weight mean diameter of 25 to 250 μm, an apparent density of 0.3 to 1.5 g/cm³, and a pore volume of 0.10 to 1.5 cm³/g, said process further comprising:
    continuously withdrawing the catalyst having coke deposited thereon from the first column;
    transferring the catalyst to a second column;
    regenerating the catalyst in the second column by treating said catalyst with a gas comprising molecular oxygen to burn or gasify the coke; and
    recycling the regenerated catalyst to the first column;

10. The process of claim 8, wherein said catalyst is prepared by impregnating said alumina particles with a solution of a decomposable vanadium compound, then drying and heating said impregnated alumina particles.

* * * * *